(12) United States Patent
Lee et al.

(10) Patent No.: US 11,452,913 B2
(45) Date of Patent: Sep. 27, 2022

(54) EXERCISE GUIDING METHOD BASED ON THE DIFFERENT FITNESS PERFORMANCE LEVELS

(71) Applicant: bOMDIC, Inc., New Taipei (TW)

(72) Inventors: Po-Chun Lee, New Taipei (TW); Jr-Wei Tsai, New Taipei (TW); Hsin-Fu Kuo, New Taipei (TW)

(73) Assignee: BOMDIC, INC., New Taipei (TW)

( * ) Notice: Subject to any disclaimer, the term of this patent is extended or adjusted under 35 U.S.C. 154(b) by 447 days.

(21) Appl. No.: 16/733,180

(22) Filed: Jan. 2, 2020

(65) Prior Publication Data
US 2021/0205661 A1    Jul. 8, 2021

(51) Int. Cl.
*A63B 24/00* (2006.01)
*A61B 5/22* (2006.01)
*G16H 20/30* (2018.01)
*A61B 5/0205* (2006.01)

(52) U.S. Cl.
CPC ........ *A63B 24/0062* (2013.01); *A61B 5/0205* (2013.01); *A61B 5/222* (2013.01); *G16H 20/30* (2018.01); *A63B 2024/0065* (2013.01); *A63B 2024/0068* (2013.01)

(58) Field of Classification Search
None
See application file for complete search history.

(56) References Cited

U.S. PATENT DOCUMENTS

2017/0249599 A1 *  8/2017  Barnes ............... G06Q 10/1095

FOREIGN PATENT DOCUMENTS

| EP | 1852062 A1 * | 11/2007 | ......... A61B 5/02438 |
| EP | 3012757 A1 * | 4/2016 | ......... A61B 5/02438 |
| WO | WO-2015069124 A1 * | 5/2015 | ........... A61B 5/0205 |

\* cited by examiner

*Primary Examiner* — Kristy A Haupt
(74) *Attorney, Agent, or Firm* — Chieh-Mei Wang (57) ABSTRACT

The present invention discloses a method for providing an exercise guiding. Determine at least one mathematical correspondence to divide a coordinate plane into a plurality of regions for defining a plurality of two-dimensional exercise training zones, wherein the coordinate plane has a first axis based on a first parameter of a fitness performance level and a second axis based on a second parameter of an exercise intensity. Transform the plurality of two-dimensional exercise training zones into a plurality of one-dimensional exercise training zones of a current value of the fitness performance level for a user having the current value of the fitness performance level. Provide the exercise guiding for the user according to the plurality of one-dimensional exercise training zones.

20 Claims, 9 Drawing Sheets

EXERCISE GUIDING METHOD BASED ON THE DIFFERENT FITNESS PERFORMANCE LEVELS

BACKGROUND OF THE INVENTION

1. Field of the Invention

The present invention relates to an exercise guiding method, and more particularly to an exercise guiding method based on the different fitness performance levels.

2. Description of Related Art

Generally, determining the personal heart-rate zones is age-based. First, compute the maximum heart rate according to the formula, such as 220 minus the user's age (unit: beats per minute (BPM)); second, each of the personal heart-rate zones is determined according to the ratio range of the maximum heart rate, and the ration range is based on the common knowledge in the exercising field.

If two users have the same age, the personal heart-rate zones of one user are the same as the personal heart-rate zones of the other user. In other words, if two users want to have the same training effect (e.g., fat-burning), the provided exercise guiding and exercise intensity is also identical. However, even if two users have the same age, the fitness performance level (e.g., $VO_{2max}$) of one user may be different from that of the other user; if two users want to have the same training effect, one user of more fitness performance level needs acuter exercise guiding and exercise intensity than the other user of less fitness performance level. Besides, the fitness performance level of the user may vary with time, so the personal heart-rate zones of the user in an early time may be different from the personal heart-rate zones of the user in a later time. Therefore, age-based personal heart-rate zones neither provide two users of the same age with the difference of exercise guiding and exercise intensity nor provide a single user with variable personal heart-rate zones.

Accordingly, the present invention proposes an exercise guiding method based on the different fitness performance levels to overcome the above-mentioned disadvantages.

SUMMARY OF THE INVENTION

In the present invention, the personal heart-rate zones of the user are determined based on his fitness performance level (e.g., $VO_{2max}$). Even if two users have the same age but have different fitness performance levels, the present invention can provide the difference of exercise guiding and exercise intensity for them when they want to have the same training effect. Besides, the personal heart-rate zones in the present invention can still provide a single user with the variable personal heart-rate zones when his fitness performance level changes. Because the personal heart-rate zones in the present invention vary with the fitness performance level of the user, the personal heart-rate zones in the present invention can precisely provide the optimal scheme in exercise guiding and exercise intensity for the user.

When determining the personal heart-rate zones of the user according to his fitness performance level, the optimal scheme in exercise guiding and exercise intensity relies on the precision of the size/location of each heart-rate zone, and the precision of the size/location of each heart-rate zone further relies on the precision of its boundary. By the algorithm implemented in the computer of the present invention, when the computer of the present invention performs operations described in claims to determine the personal heart-rate zones of the user based on his fitness performance level, largely improve the precision of the boundary of each heart-rate zone and further optimize the scheme in exercise guiding and exercise intensity.

In one embodiment, the present invention discloses a method for providing an exercise guiding. The method comprises: determining, by a processing unit, at least one mathematical correspondence to divide a coordinate plane into a plurality of regions for defining a plurality of two-dimensional exercise training zones, wherein the coordinate plane has a first axis based on a first parameter of a fitness performance level and a second axis based on a second parameter of an exercise intensity, wherein determining at least one mathematical correspondence comprises: acquiring, from a memory unit, a data set comprising at least one data subset, wherein each data subset of the at least one data subset comprises a plurality of values of the fitness performance level and a plurality of values of the exercise intensity in a state of an exercise threshold respectively corresponding to the plurality of values of the fitness performance level; and for each of the at least one mathematical correspondence, performing, by the processing unit, a calculation based on the associating data thereof comprising at least one portion of a content of the data set; transforming, by the processing unit, the plurality of two-dimensional exercise training zones into a plurality of one-dimensional exercise training zones of a current value of the fitness performance level for a user having the current value of the fitness performance level; and providing, by the outputting unit, the exercise guiding for the user according to the plurality of one-dimensional exercise training zones.

In another embodiment, the present invention discloses a method for providing an exercise guiding. The method comprises: determining, by a processing unit, a plurality of mathematical correspondences to divide a coordinate plane into a plurality of regions for defining a plurality of two-dimensional heart-rate zones, wherein the coordinate plane has a first axis based on a $VO_{2max}$ and a second axis based on a heart rate, wherein determining the plurality of mathematical correspondences comprises: acquiring, from a memory unit, a data set comprising a first data subset, a second data subset and a third data subset, wherein the first data subset comprises a plurality of first values of the $VO_{2max}$ and a plurality of values of the heart rate in the state of a $VO_{2max}$ threshold respectively corresponding to the plurality of first values of the $VO_{2max}$, the second data subset comprises a plurality of second values of the $VO_{2max}$ and a plurality of values of the heart rate in the state of a LT2 (second lactate threshold) respectively corresponding to the plurality of second values of the $VO_{2max}$, and the third data subset comprises a plurality of third values of the $VO_{2max}$ and a plurality of values of the heart rate in the state of a LT1 (first lactate threshold) respectively corresponding to the plurality of third values of the $VO_{2max}$; and for each of the plurality of mathematical correspondences, performing, by the processing unit, a calculation based on the associating data thereof comprising at least one portion of a content of the data set; transforming, by the processing unit, the plurality of two-dimensional heart-rate zones into a plurality of one-dimensional heart-rate zones of a current value of the $VO_{2max}$ for a user having the current value of the $VO_{2max}$; and providing, by the outputting unit, the exercise guiding for the user according to the plurality of one-dimensional heart-rate zones.

In another embodiment, the present invention discloses a method for providing an exercise guiding. The method comprises: determining, by a processing unit, at least one mathematical correspondence to divide a N-dimensional space into a plurality of regions for defining a plurality of N-dimensional exercise training zones, wherein N is an integer and at least three, wherein the N-dimensional space has N−1 first axes respectively based on N−1 first parameters and a second axis based on a second parameter of an exercise intensity, wherein each two first parameters of the N−1 first parameters are different and one of the N−1 first parameters is the first parameter of a fitness performance level, wherein determining at least one mathematical correspondence comprises: acquiring, from a memory unit, a data set comprising at least one data subset, wherein each data subset of the at least one data subset comprises a plurality of values of the fitness performance level and a plurality of sequences respectively corresponding to the plurality of values of the fitness performance level, wherein each of the plurality of sequences corresponds to the N−1 first parameters; and for each of the at least one mathematical correspondence, performing, by the processing unit, a calculation based on the associating data thereof comprising at least one portion of a content of the data set; transforming, by the processing unit, the plurality of N-dimensional exercise training zones into a plurality of one-dimensional exercise training zones of a current sequence of the N−1 first parameters for a user having the current sequence of the N−1 first parameters; and providing, by the outputting unit, the exercise guiding for the user according to the plurality of one-dimensional exercise training zones.

The detailed technology and above preferred embodiments implemented for the present invention are described in the following paragraphs accompanying the appended drawings for people skilled in the art to well appreciate the features of the claimed invention.

BRIEF DESCRIPTION OF THE DRAWINGS

The foregoing aspects and many of the accompanying advantages of this invention will become more readily appreciated as the same becomes better understood by reference to the following detailed description when taken in conjunction with the accompanying drawings, wherein.

DETAILED DESCRIPTION OF THE ILLUSTRATED EMBODIMENTS

The detailed explanation of the present invention is described as following. The described preferred embodiments are presented for purposes of illustrations and description and they are not intended to limit the scope of the present invention.

The first lactate threshold (LT1) is abbreviated as LT1 in the following description for simplicity. The second lactate threshold (LT2) is abbreviated as LT2 in the following description for simplicity. $VO_{2max}$ is the maximum rate of oxygen consumption measured during an incremental exercise; in other words, the rate of oxygen consumption of the user has a maximum when the user is in the state of the $VO_{2max}$ threshold.

The mathematical correspondence may describe the correlation between two parameters and provide a sufficient match between two parameters. The mathematical correspondence may be a function describing the dependence of one parameter on the other parameter. The mathematical correspondence can be estimated by a linear regression model, a non-linear regression model, or any other suitable mathematical models. Further, the mathematical correspondence may describe the correlation among three or more parameters and provide a sufficient match among three or more parameters.

One-dimensional heart-rate zones 101 are defined only using a parameter "heart rate". FIG. 1B illustrates one-dimensional heart-rate zones 101 having two heart-rate zones 101A, 101B for a $VO_{2max-1}$. FIG. 1B also illustrates one-dimensional heart-rate zones 102 having two heart-rate zones 102A, 102B for a $VO_{2max-2}$. For simplicity, take one-dimensional heart-rate zones 101 for example in the following description. The range of the heart rate of one one-dimensional heart-rate zone 101A may be different from the range of the heart rate of another one-dimensional heart-rate zone 101B. One-dimensional heart-rate zones 101 can be used to provide an exercise guiding according to an exercise profile defined by a pattern of one-dimensional heart-rate zones 101. For example, the exercise guiding provided by one 101A of one-dimensional heart-rate zones 101 is different from the exercise guiding provided by another 101B of one-dimensional heart-rate zones 101. Furthermore, one-dimensional heart-rate zones 101 are associated with monitoring the training effect of the exercise. Two-dimensional heart-rate zones 100 are defined on the coordinate plane has a X axis indicating a $VO_{2max}$ and a Y axis indicating a heart rate (see FIG. 1A). Please further see the relationship between the FIG. 1A and FIG. 1B. If two-dimensional heart-rate zones 100 are symbolized as M and one-dimensional heart-rate zones 101 are symbolized as $N_i$, $N_i$ can be regarded as an element of a set M. For any two elements $N_p$ and $N_q$ (subscript i=p, q, p is not equal to q, element $N_p$ is derived from M based on $VO_{2max-p}$ on the X axis and element $N_g$ is derived from M based on $VO_{2max-g}$ on the X axis), $VO_{2max-p}$ is not equal to $VO_{2max-g}$. If a user has a current $VO_{2max}$ value, one-dimensional heart-rate zones 101 derived from two-dimensional heart-rate zones 100 based on the current $VO_{2max}$ value on the X axis can be provided for the user to serve as the user's personal one-dimensional heart-rate zones 101. One of the terms "exercise training zones", "exertion level zones" may be substituted for the term "heart-rate zones", wherein the range of each zone is defined based on a parameter of an exercise intensity. The parameter of the exercise intensity may be heart rate, cycling cadence, speed, force, pedaling power or motion intensity. Therefore, for example, the relationship between two-dimensional exercise training zones and one-dimensional exercise training zones is similar to the foregoing description.

Figure 2:
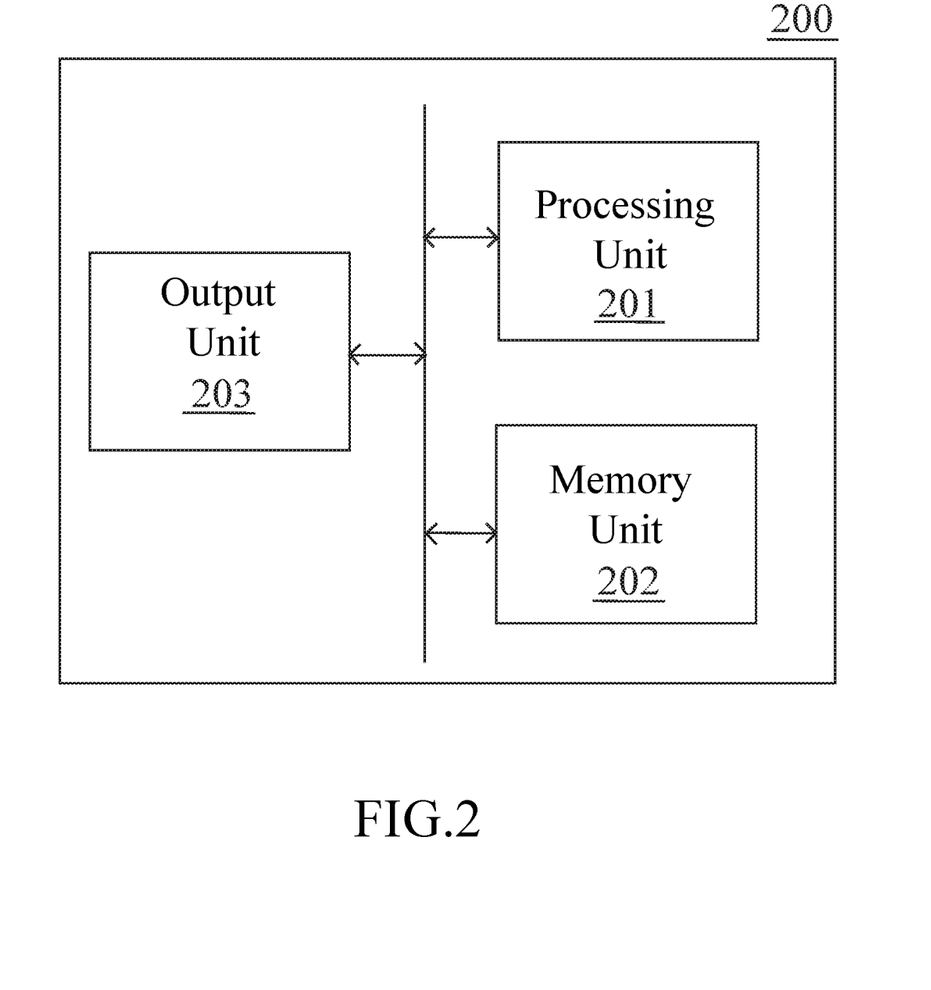
FIG. 2 illustrates a schematic block diagram of an exemplary apparatus in the present invention.

The method in the present invention can be applied in all kinds of apparatuses, such as a wrist top device. FIG. 2 illustrates a schematic block diagram of an exemplary apparatus 200 in the present invention. The apparatus 200 may comprise a processing unit 201, a memory unit 202 and an outputting unit 203. The apparatus 200 may further comprise an input unit (e.g., a senor for measuring heart rate), but it is not shown herein. The processing unit 201 may be any suitable processing device for executing software instructions, such as a central processing unit (CPU). The Memory unit 202 may include random access memory (RAM) and read only memory (ROM), but it is not limited to this case. The memory unit 202 may include any suitable non-transitory computer readable medium, such as ROM, CD-ROM, DVD-ROM and so on. Also, the non-transitory computer readable medium is a tangible medium. The non-transitory computer readable medium includes a computer program code. The memory unit 202 and the computer program code are configured with the processing unit 201 to cause the apparatus 200 to perform desired operations (e.g., operations listed in claims). The outputting unit 203 may be a display for displaying exercise guiding or exercise index.

Figure 3:
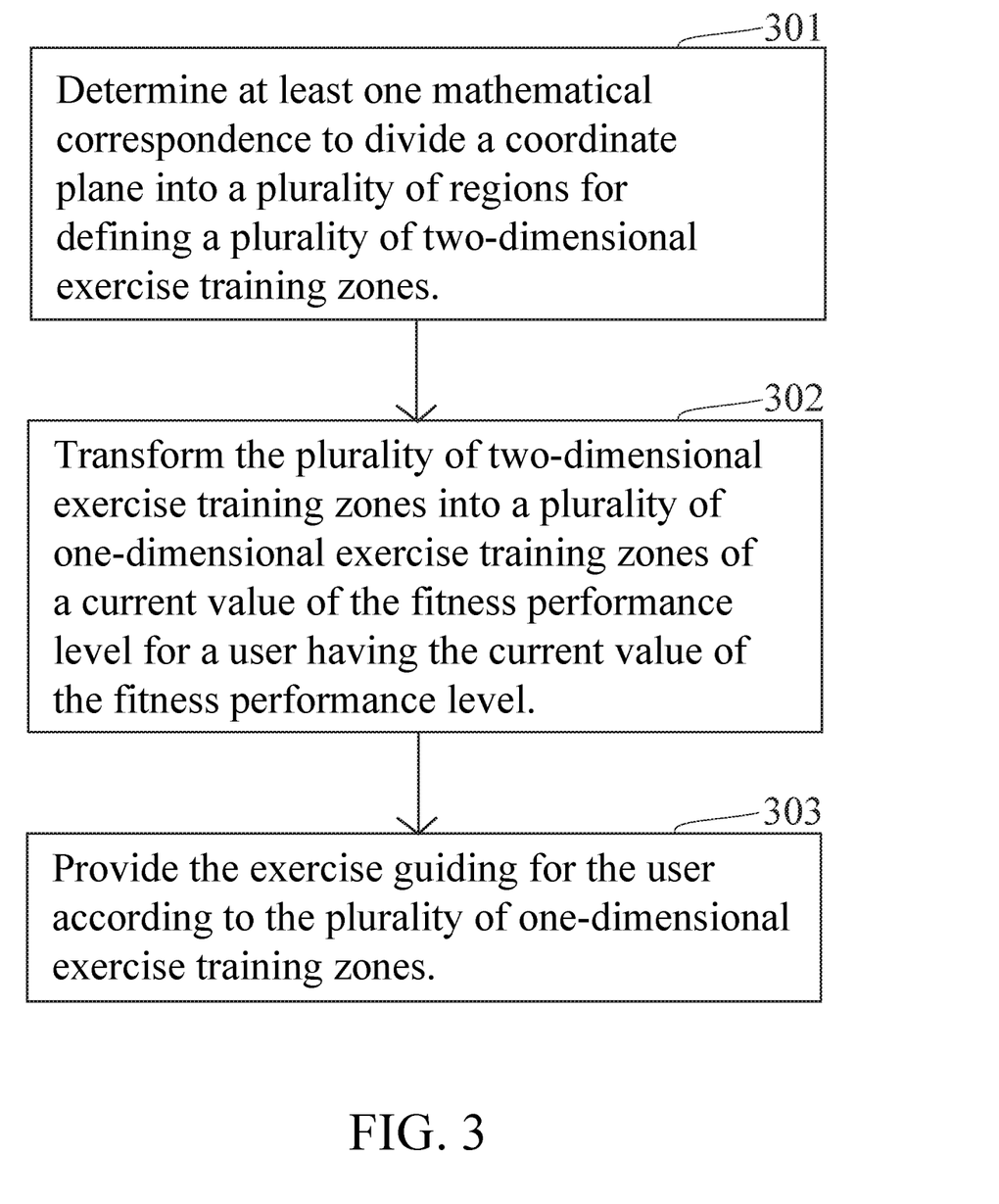
FIG. 3 illustrates a process for providing an exercise guiding in the present invention.

FIG. 3 illustrates a process for providing an exercise guiding in the present invention. The process in FIG. 3 starts in step 301: determine at least one mathematical correspondence to divide a coordinate plane into a plurality of regions for defining a plurality of two-dimensional exercise training zones (by the processing unit). The coordinate plane has a first axis based on a first parameter of a fitness performance level and a second axis based on a second parameter of an exercise intensity. The fitness performance level may include health-related fitness and sport/skill-related fitness which can be also improved by engaging physical activities or training. For example, the first parameter of the fitness performance level may be $VO_{2max}$ or $MET_{max}$ (maximum oxygen uptake capacity relative to resting oxygen consumption: equal to $VO_{2max}/3.5$), and $VO_{2max}$ is preferred. Generally, a unit of the $VO_{2max}$ can be represented in an absolute way, such as oxygen uptake (ml/min), or in a relative way, such as oxygen uptake based on weight (ml/kg/min). The second parameter of the exercise intensity may be heart rate, cycling cadence, speed, force, pedaling power or motion intensity. In this example, the second parameter of the exercise intensity is a heart rate for the sake of simplicity. Generally, a unit of the heart rate is beats per minute (BPM). The heart rate may be in the form of the percentage of the heart rate reserve (% HRR). The percentage of the heart rate reserve represents the ratio of the difference between the heart rate and the resting heart rate to the difference between the maximum heart rate and the resting heart rate. The shape determined by the mathematical correspondence may be a boundary between the two adjacent regions. The shape determined by the mathematical correspondence may be also a boundary of the two adjacent two-dimensional exercise training zones. The shaped determined by each of the at least one mathematical correspondence may ascend relative to the first axis as the first axis extends along a positive direction thereof. Optionally, the shape determined by each of the at least one mathematical correspondence may ascend relative to the first axis as the first axis extends along a positive direction in a certain range of the fitness performance level. The shape may be a straight line, a curve or any other suitable shape. The number of the two-dimensional exercise training zones may be equal to the number of the divided regions. The number of the two-dimensional exercise training zones may be less than the number of the divided regions according to the fitness performance level and the exercise requirement of the user.

Figure 4:
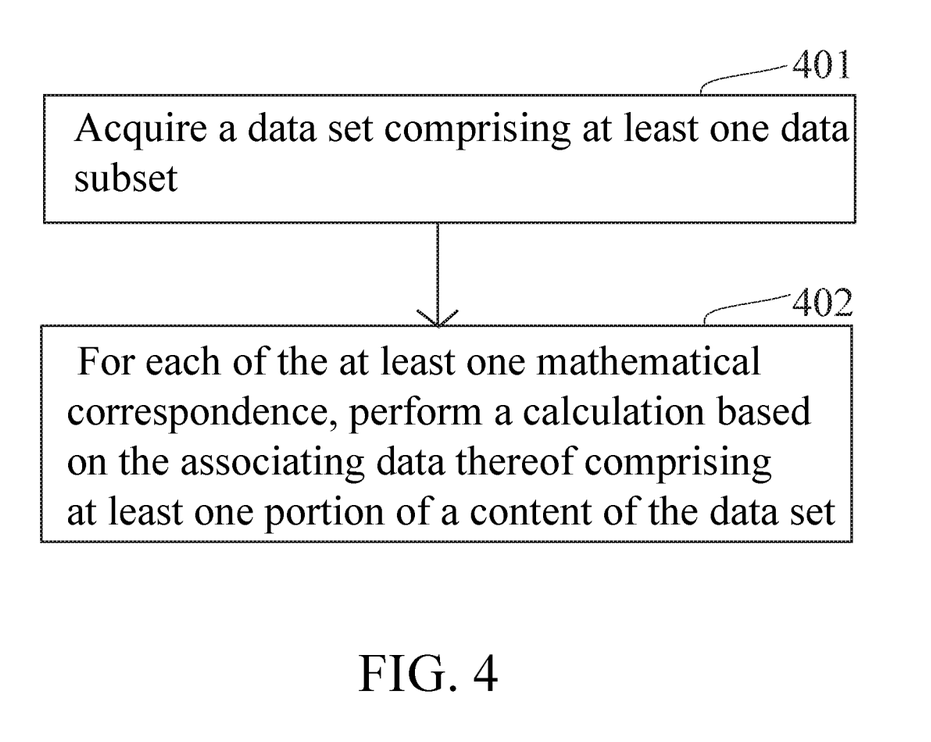
FIG. 4 illustrates a process for determining at least one mathematical correspondence in step 301 of FIG. 3.

FIG. 4 illustrates a process for determining at least one mathematical correspondence in step 301 of FIG. 3. The process starts in step 401: acquire a data set comprising at least one data subset (from a memory unit). Each data subset of the at least one data subset comprises a plurality of values of the fitness performance level (e.g., $VO_{2max}$) and a plurality of values of the exercise intensity (e.g., heart rate) in a state of an exercise threshold respectively corresponding to the plurality of values of the fitness performance level. The data set may be acquired from a group of people or a single person, or the values of the fitness performance level (e.g., $VO_{2max}$) may be acquired from a group of people or a single person. In the first example of the data subset, the exercise threshold is a $VO_{2max}$ threshold and the data subset is acquired in the state of the $VO_{2max}$ threshold. The data subset comprises a plurality of values of the $VO_{2max}$ and a plurality of values of the heart rate in the state of a $VO_{2max}$ threshold respectively corresponding to the plurality of values of the $VO_{2max}$. For example, see FIG. 1A, the data subset includes five triangular coordinates $(X_i, Y_i)$, i=1 to 5; $X_i$ represents the value of $VO_{2max}$ (fitness performance level) which may be acquired from a group of people or a single person, and $Y_i$ represents the value of the heart rate in the state of the $VO_{2max}$ threshold. In the second example of the data subset, the exercise threshold is a LT2 and the data subset is acquired in the state of the LT2. For example, see FIG. 1A, the data subset includes five circular coordinates $(X_j, Y_j)$, j=1 to 5; $X_j$ represents the value of $VO_{2max}$ which may be acquired from a group of people or a single person, and $Y_j$ represents the value of the heart rate in the state of the LT2. In the third example of the data subset, the exercise threshold is a LT1 and the data subset is acquired in the state of the LT1. For example, see FIG. 1A, the data subset includes five square coordinates $(X_k, Y_k)$, k=1 to 5; $X_k$ represents the value of $VO_{2max}$ which may be acquired from a group of people or a single person, and $Y_k$ represents the value of heart rate in the state of the LT1. However, the data subset is not limited to the foregoing case and the exercise threshold may be user-defined to acquire the desired data subset.

In step 402: for each of the at least one mathematical correspondence, perform a calculation based on the associating data thereof comprising at least one portion of a content of the data set (by the processing unit). For each of the at least one mathematical correspondence, the calculation may be performed based on the associating data thereof comprising at least one data subset of the data set. The calculation performed for the mathematical correspondence can be estimated by a linear regression model, a non-linear regression model, or any other suitable mathematical models. The least squares method may be applied, and the detailed description is omitted herein. The associating data of the mathematical correspondence used for performing the calculation may have multiple ways.

In one way, one mathematical correspondence is associated with only one data subset. Preferably, the data subset is acquired in the state of the $VO_{2max}$ threshold (i.e., the exercise threshold is a $VO_{2max}$ threshold); for example, see FIG. 1A, the data subset in the state of the $VO_{2max}$ threshold includes five triangular coordinates $(X_i, Y_i)$, i=1 to 5. The mathematical correspondence 111 is associated with the data subset acquired in the state of the $VO_{2max}$ threshold. Also, the value of the exercise intensity in the state of the $VO_{2max}$ threshold of a person having a current value of the fitness performance level (e.g., $VO_{2max}$) can be estimated by the mathematical correspondence 111 associated with the data subset acquired in the state of the $VO_{2max}$ threshold or interpolation/extrapolation of the data subset acquired in the state of the $VO_{2max}$ threshold.

Figure 1A:
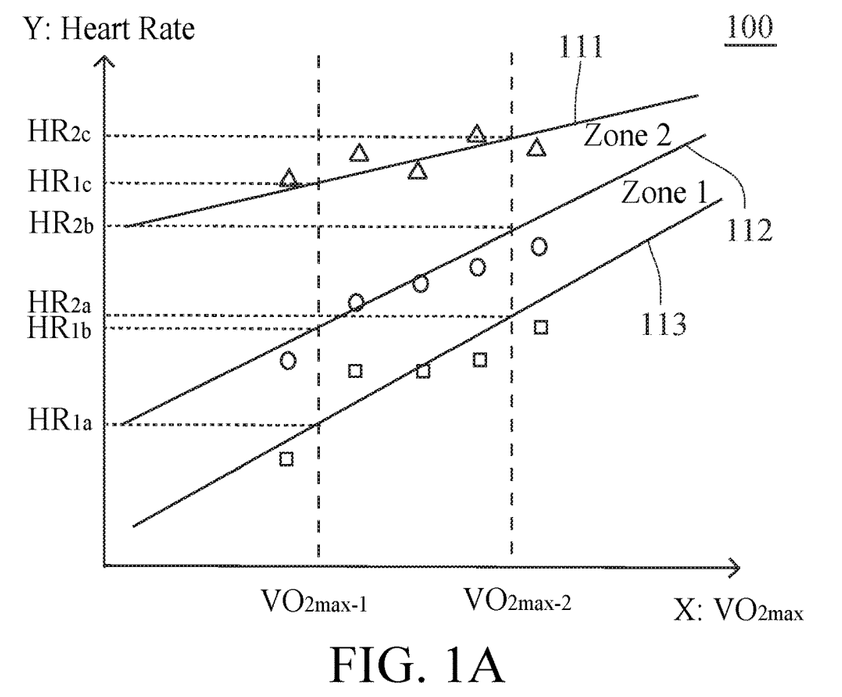
FIG. 1A illustrates two-dimensional heart-rate zones defined on the coordinate plane having a X axis indicating a $VO_{2max}$ and a Y axis indicating a heart rate.
Figure 1B:
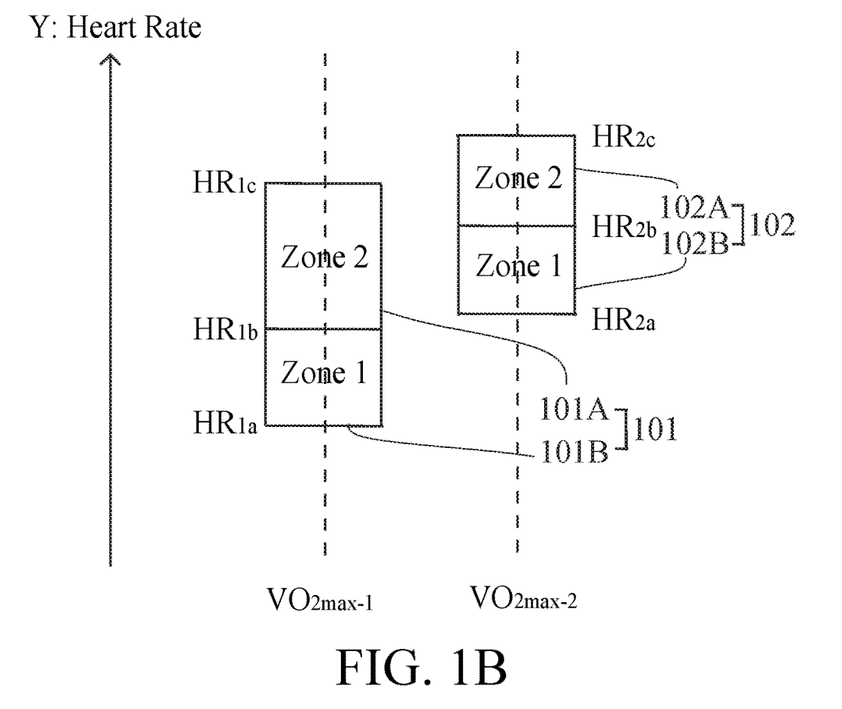
FIG. 1B illustrates one-dimensional heart-rate zones having two heart-rate zones for a $VO_{2max}$.

Optionally, the data subset is acquired in the state of the LT2 (i.e., the exercise threshold is a LT2); for example, see FIG. 1A, the data subset includes five circular coordinates $(X_j, Y_j)$, j=1 to 5. The mathematical correspondence 112 is associated with the data subset acquired in the state of the LT2. Also, the value of the exercise intensity in the state of the LT2 of a person having a current value of the fitness performance level (e.g., $VO_{2max}$) can be estimated by the mathematical correspondence 112 associated with the data subset acquired in the state of the LT2 or interpolation/extrapolation of the data subset acquired in the state of the LT2.

Optionally, the data subset is acquired in the state of the LT1 (i.e., the exercise threshold is a LT1), for example, see FIG. 1A, the data subset includes five square coordinates $(X_k, Y_k)$, k=1 to 5. The mathematical correspondence 113 is associated with the data subset acquired in the state of the LT1. Also, the value of the exercise intensity in the state of the LT1 of a person having a current value of the fitness performance level (e.g., $VO_{2max}$) can be estimated by the mathematical correspondence 113 with the data subset acquired in the state of the LT1 or interpolation/extrapolation of the data subset acquired in the state of the LT1.

The above method can be also applied in estimating the value of the exercise intensity in the state of any other exercise threshold (e.g., anaerobic threshold, aerobic threshold or any suitable exercise threshold which is easy to measure, observe or judge) of a person having a current value of the fitness performance level (e.g., $VO_{2max}$).

Figure 5A:
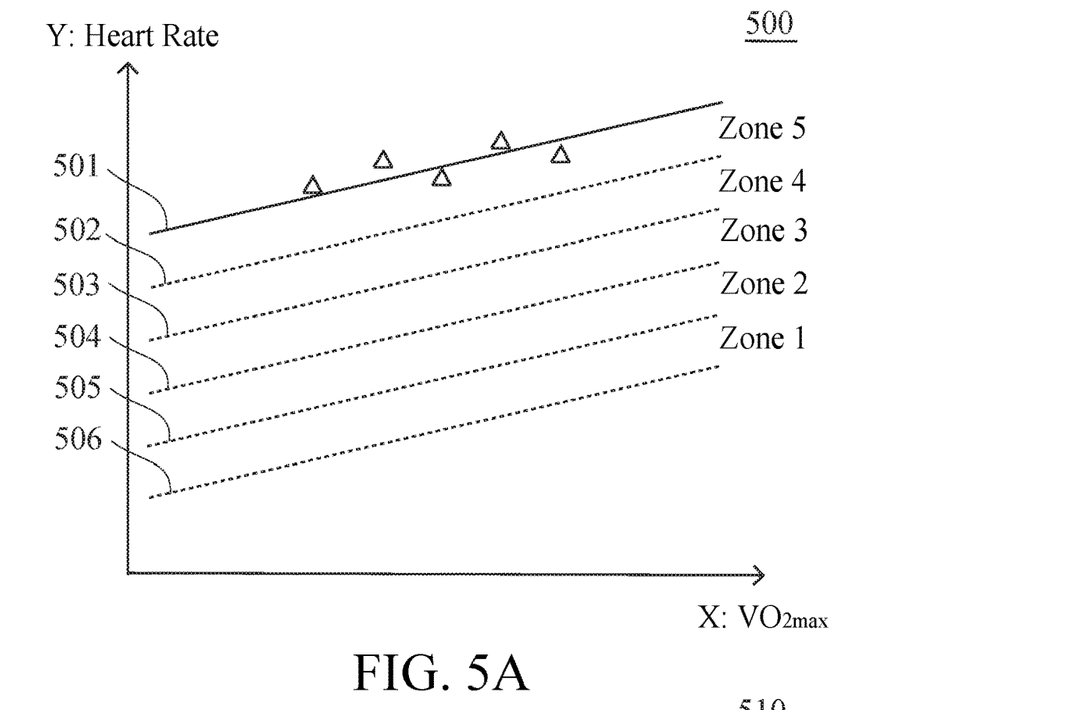
FIG. 5A illustrates that the remaining boundaries are determined according to the finished mathematical correspondence after finishing the mathematical correspondence associated with the data subset acquired in the state of the $VO_{2max}$ threshold to determine one boundary.
Figure 5B:
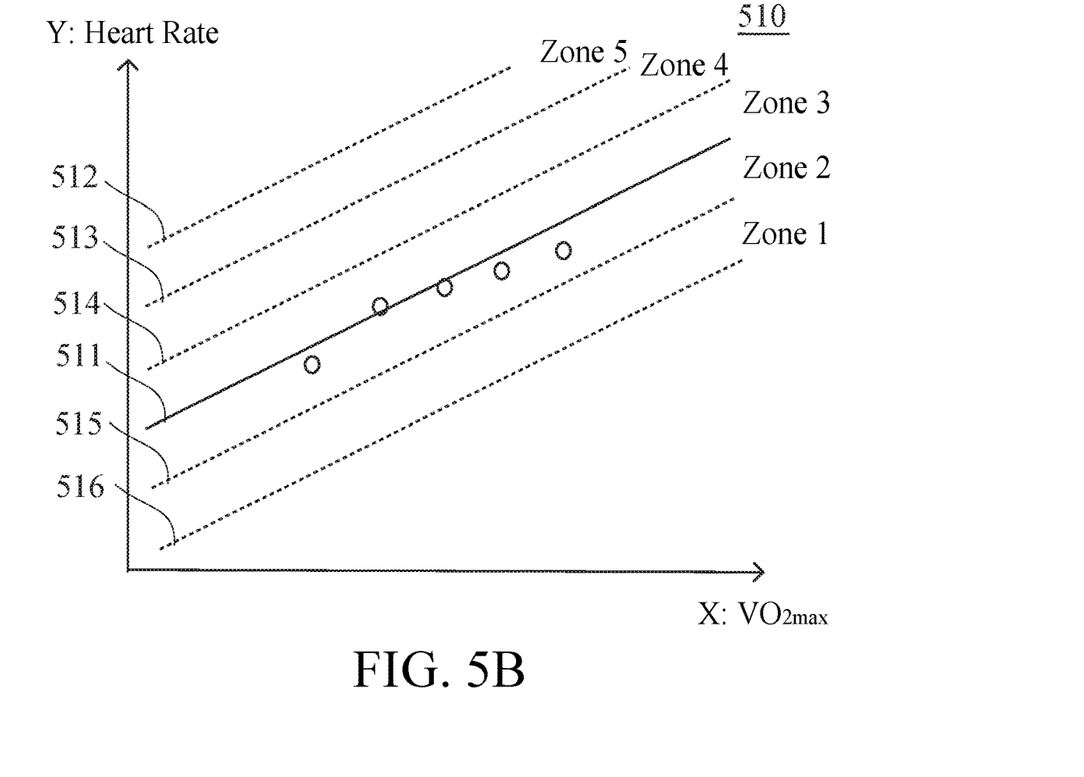
FIG. 5B illustrates that the remaining boundaries are determined according to the finished mathematical correspondence after finishing the mathematical correspondence associated with the data subset acquired in the state of the LT2 (second lactate threshold) to determine one boundary.
Figure 5C:
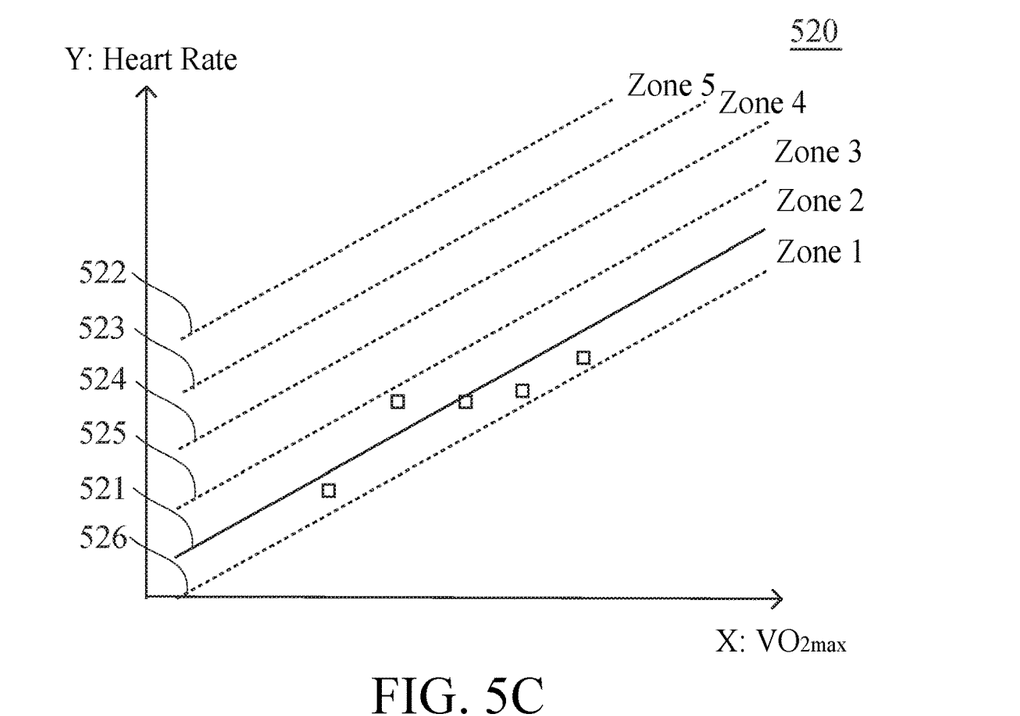
FIG. 5C illustrates that the remaining boundaries are determined according to the finished mathematical correspondence after finishing the mathematical correspondence associated with the data subset acquired in the state of the LT1 (first lactate threshold) to determine one boundary.

In one embodiment, after finishing one mathematical correspondence associated with one data subset acquired in the state of a specific exercise threshold to determine one of the boundaries of the two-dimensional exercise training zones, the remaining boundaries can by determined according to the finished mathematical correspondence. For example, the remaining boundaries can be determined according to the finished mathematical correspondence plus/minus the ratio range of the common knowledge in the exercising field or any other suitable technology. The ratio range may be based on the maximum heart rate, but it is not limited to this case. Preferably, the state of the specific exercise threshold is the state of the $VO_{2max}$ threshold. For example, see two-dimensional heart-rate zones 500 in FIG. 5A, after finishing the mathematical correspondence 501 associated with the data subset acquired in the state of the $VO_{2max}$ threshold to determine the boundary 501, the remaining boundaries 502, 503, 504, 505, 506 may be determined according to the heart rate TOP-HR of the finished mathematical correspondence 501 minus 10% of the heart rate TOP-HR, 20% of the heart rate TOP-HR, 30% of the heart rate TOP-HR, 40% of the heart rate TOP-HR and 50% of the heart rate TOP-HR. In other words, the ratio range of Zone 1, Zone 2, Zone 3, Zone 4 and Zone 5 is respectively 50%-60% of the heart rate TOP-HR, 60%-70% of the heart rate TOP-HR, 70%-80% of the heart rate TOP-HR, 80%-90% of the heart rate TOP-HR and 90%-100% of the heart rate TOP-HR. The ratio range of each two-dimensional heart-rate zone may be also different; for example, the ratio range of Zone 1, Zone 2, Zone 3, Zone 4 and Zone 5 is respectively 40%-54% of the heart rate TOP-HR, 54%-67% of the heart rate TOP-HR, 67%-79% of the heart rate TOP-HR, 79%-90% of the heart rate TOP-HR and 90%-100% of the heart rate TOP-HR. Optional, the state of the specific exercise threshold is the state of the LT2. See two-dimensional heart-rate zones 510 in FIG. 5B, after finishing the mathematical correspondence 511 associated with the data subset acquired in the state of the LT2 to determine one boundary 511, the remaining boundaries 512, 513, 514, 515, 516 may be determined according to the finished mathematical correspondence 511. The ratio range of each two-dimensional heart-rate zone may be the same or different. Optional, the state of the specific exercise threshold is the state of the LT1. See two-dimensional heart-rate zones 520 in FIG. 5C, after finishing the mathematical correspondence 521 associated with the data subset acquired in the state of the LT1 to determine one boundary 521, the remaining boundaries 522, 523, 524, 525, 526 may be determined according to the finished mathematical correspondence 521. The ratio range of each two-dimensional heart-rate zone may be the same or different.

Figure 6:
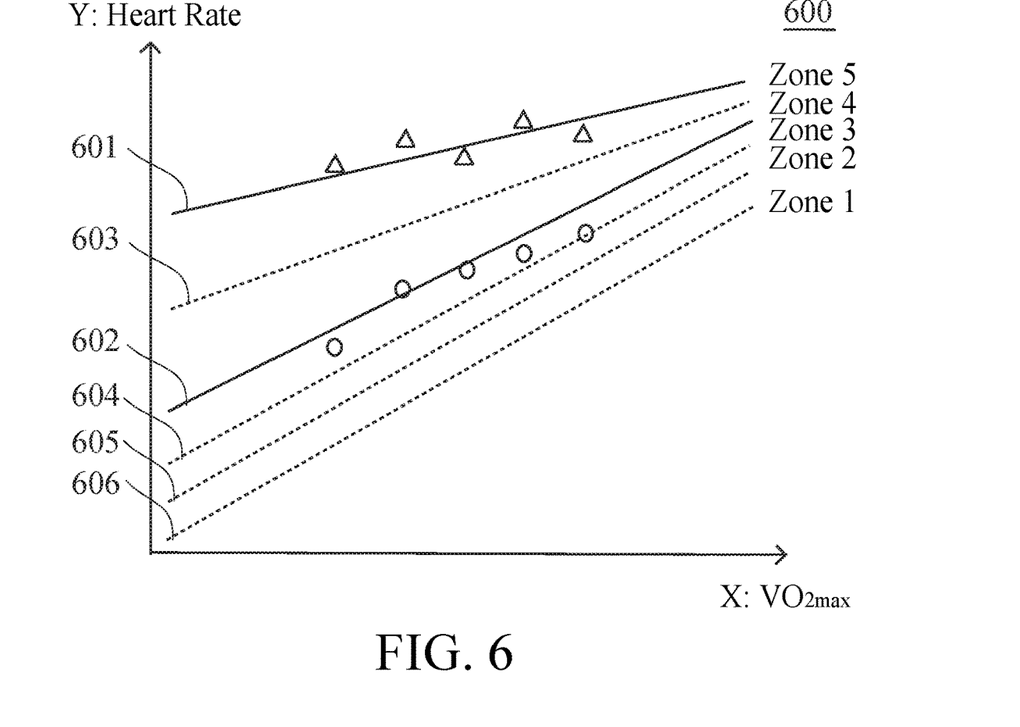
FIG. 6 illustrates that the remaining boundaries are determined according to the finished first mathematical correspondence and the finished second mathematical correspondence after finishing the first mathematical correspondence associated with the first data subset acquired in the state of the $VO_{2max}$ threshold and the second mathematical correspondence associated with the second data subset acquired in the state of the LT2 (second lactate threshold) to determine two of the boundaries.

In one embodiment, after finishing a first mathematical correspondence associated with a first data subset acquired in the state of a first exercise threshold and a second mathematical correspondence associated with a second data subset acquired in the state of a second exercise threshold to determine two of the boundaries of the two-dimensional exercise training zones, the remaining boundaries can by determined according to the finished first mathematical correspondence and the finished second mathematical correspondence. For example, the remaining boundaries can be determined according the finished first mathematical correspondence and the finished second mathematical correspondence plus/minus the ratio range of the common knowledge in the exercising field or any other suitable technology. The value of the exercise intensity in the state of the exercise threshold corresponding to the first data subset is larger than the value of the exercise intensity in the state of the exercise threshold corresponding to the second data subset if the exercise threshold corresponding to the first data subset and the exercise threshold corresponding to the second data subset are based on the same value of the fitness performance level. Preferably, the exercise threshold corresponding to the first data subset is a $VO_{2max}$ threshold. Optionally, the exercise threshold corresponding to the first data subset is a $VO_{2max}$ threshold and the exercise threshold corresponding to the second data subset is a LT2. For example, see FIG. 6, after finishing the first mathematical correspondence 601 associated with the first data subset acquired in the state of the $VO_{2max}$ threshold and the second mathematical correspondence 602 associated with the second data subset acquired in the state of the LT2 to determine two of the boundaries, the remaining boundaries 603, 604, 605, 606 can be determined according to the finished first mathematical correspondence 601 and the finished second mathematical correspondence 602. The ratio range of each two-dimensional heart-rate zone may be the same or different.

Figure 7A:
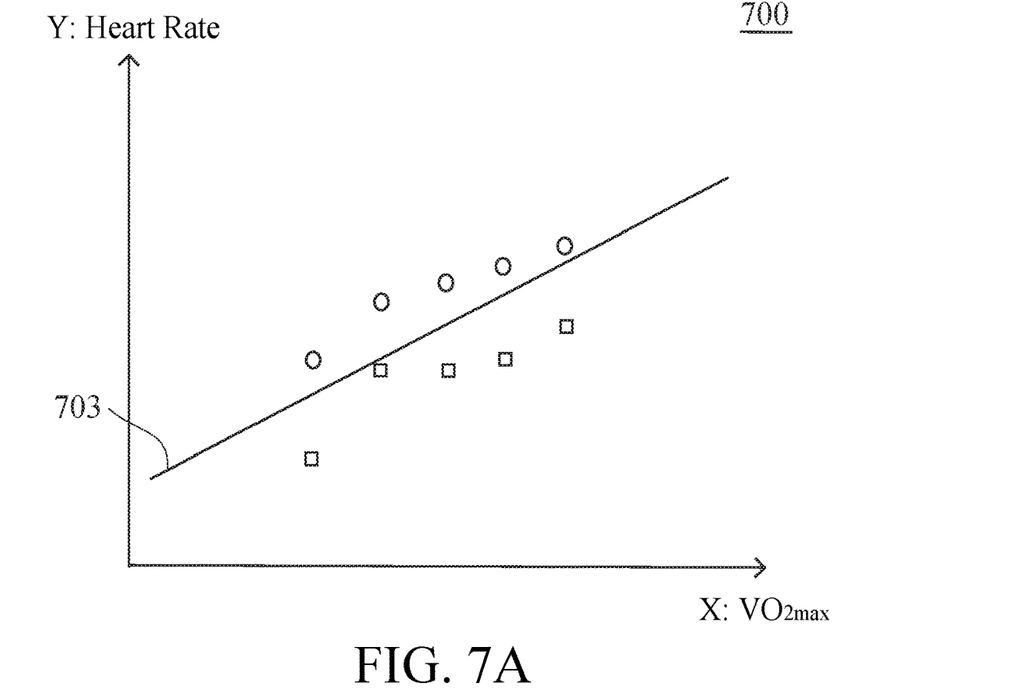
FIG. 7A illustrates that the calculation for the mathematical correspondence is performed directly based on a combination of the second data subset acquired in the state of the LT2 (second lactate threshold) and the third data subset acquired in the state of the LT1 (first lactate threshold)
Figure 7B:
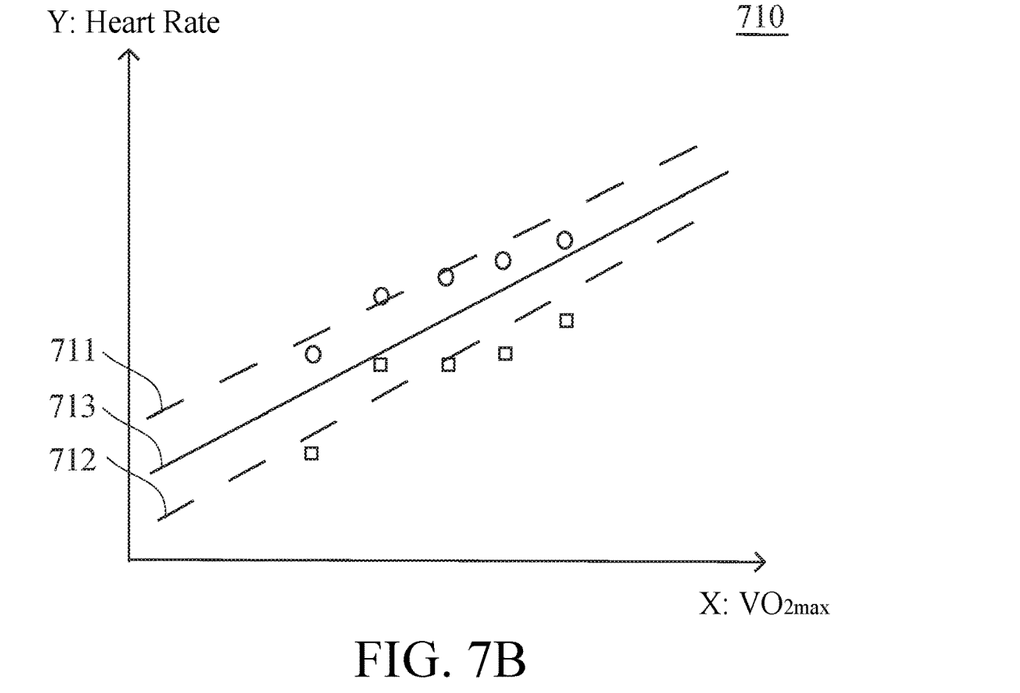
FIG. 7B illustrates that the calculation for the mathematical correspondence is performed indirectly based on a combination of the second data subset acquired in the state of the LT2 (second lactate threshold) and the third data subset acquired in the state of the LT1 (first lactate threshold)

In another way, one the mathematical correspondence is associated with multiple data subsets. The multiple data subsets may comprise at least two data subsets of the first data subset acquired in the state of the $VO_{2max}$ threshold, the second data subset acquired in the state of the LT2 and the third data subset acquired in the state of the LT1. FIG. 7A and FIG. 7B illustrate the mathematical correspondence (solid line) determined based on a combination of the second data subset acquired in the state of the LT2 and the third data subset acquired in the state of the LT1. In one embodiment, the first data subset acquired in the state of the $VO_{2max}$ threshold and the second data subset acquired in the state of the LT2 can be used in FIG. 7A and FIG. 7B. In another embodiment, the first data subset acquired in the state of the $VO_{2max}$ threshold and the third data subset acquired in the state of the LT1 can be also used in FIG. 7A and FIG. 7B.

In FIG. 7A, the calculation (e.g., a linear regression model, a non-linear regression model, or any other suitable mathematical models) for the mathematical correspondence (solid line) 703 may be performed directly based on a combination of the second data subset acquired in the state of the LT2 and the third data subset acquired in the state of the LT1.

In FIG. 7B, the calculation for the mathematical correspondence (solid line) 713 may be performed indirectly based on a combination of the second data subset acquired in the state of the LT2 and the third data subset acquired in the state of the LT1. For example, after finishing one initial mathematical correspondence (long dashed line) 711 associated with the second data subset acquired in the state of the LT2 and another mathematical correspondence (long dashed line) 712 associated with the third data subset acquired in the state of the LT1, the mathematical correspondence (solid line) 713 can be determined based on the initial mathematical correspondence (long dashed line) 711 and the initial mathematical correspondence (long dashed line) 712. The mathematical correspondence 713 may be in the middle location between the initial mathematical correspondence 711 and the initial mathematical correspondence 712. The mathematical correspondence 713 may be between the initial mathematical correspondence 711 and the initial mathematical correspondence 712 and closer to one of the initial mathematical correspondence 711 and the initial mathematical correspondence 712 based on the exercise guiding for the user.

Figure 8:
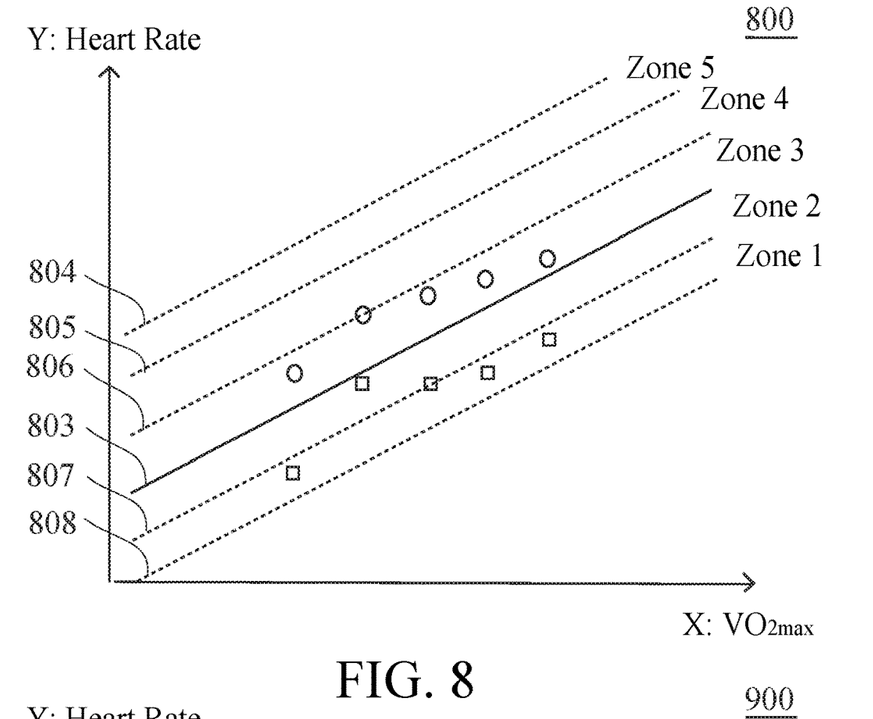
FIG. 8 illustrates that the remaining boundaries are determined according to the finished mathematical correspondence after finishing the mathematical correspondence associated with a combination of the second data subset acquired in the state of the LT2 (second lactate threshold) and the third data subset acquired in the state of the LT1 (first lactate threshold)

FIG. 8 illustrates that the remaining boundaries 804, 805, 806, 807, 808 are determined according to the finished mathematical correspondence 803 after finishing the mathematical correspondence 803 (similar to the mathematical correspondence 703 in FIG. 7A or the mathematical correspondence 713 in FIG. 7B) associated with a combination of the second data subset acquired in the state of the LT2 and the third data subset acquired in the state of the LT1. The ratio range of each two-dimensional heart-rate zone may be the same or different.

Figure 9:
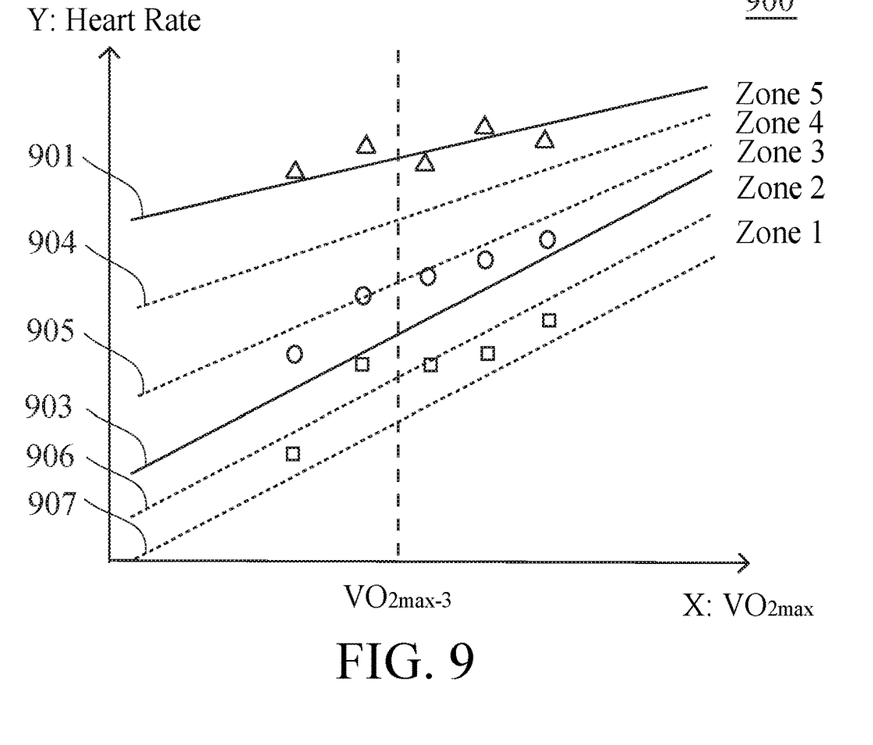
FIG. 9 illustrates that the remaining boundaries are determined according to the finished two mathematical correspondences after finishing the mathematical correspondence associated with the first data subset acquired in the state of the $VO_{2max}$ threshold and the mathematical correspondence associated with a combination of the second data subset acquired in the state of the LT2 (second lactate threshold) and the third data subset acquired in the state of the LT1 (first lactate threshold)

FIG. 9 illustrates that the remaining boundaries 904, 905, 906, 907 are determined according to the finished two mathematical correspondences 901, 903 after finishing the mathematical correspondence 901 (similar to the mathematical correspondence 501 in FIG. 5A) and the mathematical correspondence 903 (similar to the mathematical correspondence 703 in FIG. 7A or the mathematical correspondence 713 in FIG. 7B). The mathematical correspondence 901 is associated with the data subset acquired in the state of the $VO_{2max}$ threshold, and the mathematical correspondence 903 is associated with a combination of the second data subset acquired in the state of the LT2 and the third data subset acquired in the state of the LT1. The ratio range of each two-dimensional heart-rate zone may be the same or different.

The remaining boundaries can be determined according to the ratio range of the common knowledge in the exercising field or any other suitable technology like FIGS. 5A to 5C and FIG. 6, so it is not described in detail therein.

Determining at least one mathematical correspondence in step 301 may further comprise modifying a first portion more than a first threshold value of the fitness performance level of each mathematical correspondence. For example, the first portion more than the first threshold value of the fitness performance level of the mathematical correspondence may be modified to have a smaller average slope than that which is not modified. Determining at least one mathematical correspondence in step 301 may further comprise modifying a second portion less than a second threshold value of the fitness performance level of each mathematical correspondence. For example, the second portion less than the second threshold value of the fitness performance level of the mathematical correspondence may be modified to have a smaller average slope than that which is not modified. Determining at least one mathematical correspondence may further comprise modifying a first portion more than a first threshold value of the fitness performance level and a second portion less than a second threshold value of the fitness performance level of each mathematical correspondence. For example, the first portion more than the first threshold value of the fitness performance level of the mathematical correspondence may be modified to have a smaller average slope than that which is not modified, and the second portion less than the second threshold value of the fitness performance level of the mathematical correspondence may be modified to have a smaller average slope than that which is not modified.

In another embodiment, the mathematical correspondence is associated with a portion of one data subset. For example, a portion of one data subset includes four triangular coordinates $(X_i, Y_i)$, i=1 to 4; $X_i$ represents the value of $VO_{2max}$ and $Y_i$ represents the value of the heart rate in the state of the $VO_{2max}$ threshold. In another embodiment, the mathematical correspondence is associated with a portion of one data subset and a portion of another data subset. For example, a portion of one data subset includes four triangular coordinates $(X_i, Y_i)$, i=1 to 4, $X_i$ represents the value of $VO_{2max}$ and $Y_i$ represents the value of the heart rate in the state of the $VO_{2max}$ threshold; a portion of another data subset includes three circular coordinates $(X_j, Y_j)$, j=1 to 3; $X_j$ represents the value of $VO_{2max}$ and $Y_j$ represents the value of the heart rate in the state of the LT2. In another embodiment, the mathematical correspondence is associated with one data subset and a portion of another data subset. For example, one data subset includes five triangular coordinates $(X_i, Y_i)$, i=1 to 5, $X_i$ represents the value of $VO_{2max}$ and $Y_i$ represents the value of the heart rate in the state of the $VO_{2max}$ threshold; a portion of another data subset includes three circular coordinates $(X_j, Y_j)$, j=1 to 3; $X_j$ represents the value of $VO_{2max}$ and $Y_j$ represents the value of the heart rate in the state of the LT2.

From the foregoing description, the precision of the boundary of each exercise training zone or heart-rate zone depends on the relationship between at least one mathematical correspondence and the associating data thereof. The more the number of the data subsets is, the more precise the boundary of each exercise training zone or heart-rate zone is defined. The more the number of the mathematical correspondences is, the more precise each of at least one remaining boundary is defined according to at least one predetermined boundary associated with the mathematical correspondences. By the algorithm implemented in the computer of the present invention, when the computer of the present invention performs operations described in claims to determine the personal heart-rate zones of the user based on his fitness performance level, largely improve the precision of the boundary of each exercise training zone or heart-rate zone and further optimize the optimal scheme in exercise guiding and exercise intensity.

Figure 10:
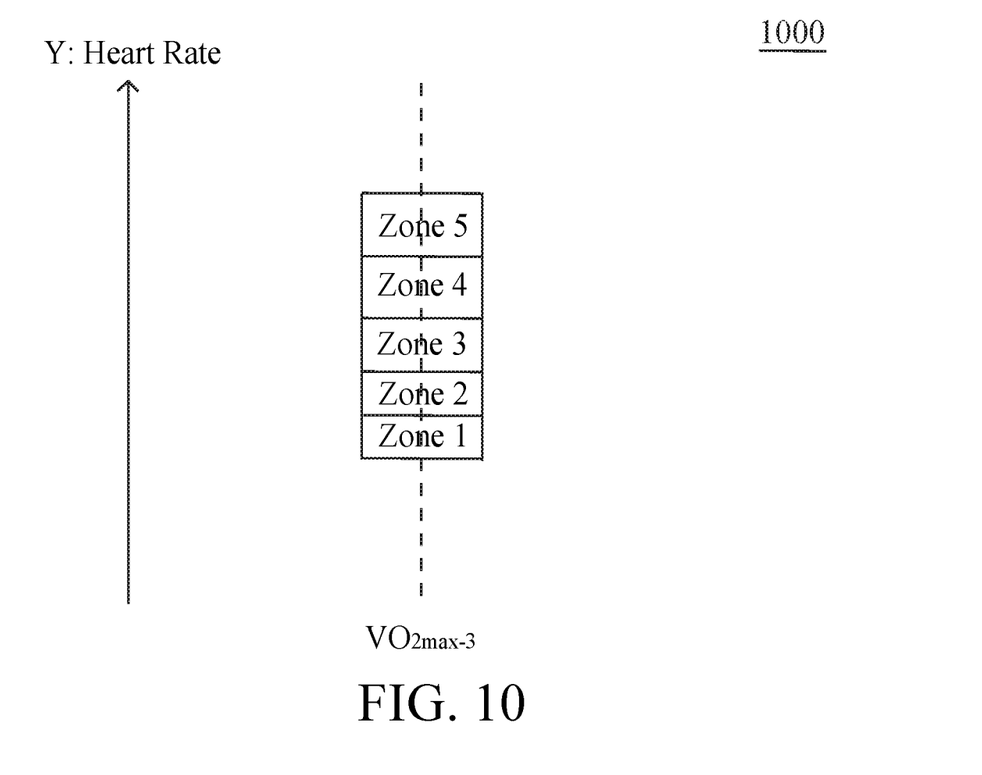
FIG. 10 illustrates one-dimensional exercise training zones derived from two-dimensional exercise training zones in FIG. 9.

Please refer back to FIG. 3. In step 302: subsequently transform the plurality of two-dimensional exercise training zones into a plurality of one-dimensional exercise training zones of a current value of the fitness performance level for a user having the current value of the fitness performance level (by the processing unit). The transformation relationship between two-dimensional exercise training zones 900 and one-dimensional exercise training zones 1000 can be seen in FIG. 9 and FIG. 10. The transformation relationship between two-dimensional exercise training zones 100 and one-dimensional exercise training zones 101 can be also seen in FIG. 1A and FIG. 1B. Finally, in step 303: provide the exercise guiding for the user according to the plurality of one-dimensional exercise training zones (by the outputting unit).

Please refer back to FIG. 1A and FIG. 1B. The present invention determines the mathematical correspondence 112 associated with the data subset acquired in the state of the LT2 and the mathematical correspondence 113 associated with the data subset acquired in the state of the LT1 to precisely estimates the location of Zone 1. For the exercise guiding provided in Zone 1, a person having $VO_{2max-2}$ can acquire the optimal exercise guiding between $HR_{2a}$ and $HR_{2b}$ rather than acquire the incorrect exercise guiding between $HR_{1a}$ and $HR_{1b}$ due to the mistaken $VO_{2max-1}$ (The mistaken $VO_{2max-1}$ may result from age-based personal heart-rate zones or the $VO_{2max}$ varying with time).

The foregoing concept of providing an exercise guiding can be extended to transforming a plurality of N-dimensional exercise training zones into a plurality of one-dimensional exercise training zones of a current sequence of the N−1 first parameters for a user having the current sequence of the N−1 first parameters.

The method is concretely listed as below:

The method comprises: determining, by a processing unit, at least one mathematical correspondence to divide a N-dimensional space into a plurality of regions for defining a plurality of N-dimensional exercise training zones, wherein N is an integer and at least three, wherein the N-dimensional space has N−1 first axes respectively based on N−1 first parameters and a second axis based on a second parameter of an exercise intensity, wherein each two first parameters of N−1 first parameters are different, wherein determining at least one mathematical correspondence comprises: acquiring, from a memory unit, a data set comprising at least one data subset, wherein each data subset of the at least one data subset comprises a plurality of values of the fitness performance level and a plurality of sequences respectively corresponding to the plurality of values of the fitness performance level, wherein each of the plurality of sequences corresponds to the N−1 first parameters; and for each of the at least one mathematical correspondence, performing, by the processing unit, a calculation based on the associating data thereof comprising at least one portion of a content of the data set; transforming, by the processing unit, the plurality of N-dimensional exercise training zones into a plurality of one-dimensional exercise training zones of a current sequence of the N−1 first parameters for a user having the current sequence of the N−1 first parameters; and providing, by the outputting unit, the exercise guiding for the user according to the plurality of one-dimensional exercise training zones.

Preferably, one of the N−1 first parameters is the first parameter of a fitness performance level. The first parameter of the fitness performance level may be $VO_{2max}$ or $MET_{max}$, and $VO_{2max}$ is preferred.

The above disclosure is related to the detailed technical contents and inventive features thereof. People skilled in the art may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for providing an exercise guiding, comprising:
   determining, by a processing unit, at least one mathematical correspondence to divide a coordinate plane into a plurality of regions for defining a plurality of two-dimensional exercise training zones, wherein the coordinate plane has a first axis based on a first parameter of a fitness performance level and a second axis based on a second parameter of an exercise intensity, wherein determining at least one mathematical correspondence comprises:
      acquiring, from a memory unit, a data set comprising at least one data subset, wherein each data subset of the at least one data subset comprises a plurality of values of the fitness performance level and a plurality of values of the exercise intensity in a state of an exercise threshold respectively corresponding to the plurality of values of the fitness performance level; and for each of the at least one mathematical correspondence, performing, by the processing unit, a calculation based on the associating data thereof comprising at least one portion of a content of the data set;

transforming, by the processing unit, the plurality of two-dimensional exercise training zones into a plurality of one-dimensional exercise training zones of a current value of the fitness performance level for a user having the current value of the fitness performance level; and providing, by the outputting unit, the exercise guiding for the user according to the plurality of one-dimensional exercise training zones.

2. The method according to claim 1, wherein determining at least one mathematical correspondence further comprises modifying at least one of a first portion more than a first threshold value of the fitness performance level and a second portion less than a second threshold value of the fitness performance level of each mathematical correspondence.

3. The method according to claim 1, wherein a shaped determined by each of the at least one mathematical correspondence ascends relative to the first axis as the first axis extends along a positive direction thereof.

4. The method according to claim 1, wherein a shaped determined by each of the at least one mathematical correspondence ascends relative to the first axis as the first axis extends along a positive direction thereof from a first threshold value of the fitness performance level to a second threshold value of the fitness performance level.

5. The method according to claim 1, wherein the calculation is performed based on the associating data thereof comprising at least one data subset of the data set.

6. The method according to claim 1, wherein the data set is acquired from a group of people.

7. The method according to claim 1, wherein the data set is acquired from a single person.

8. The method according to claim 1, wherein the first parameter of the fitness performance level is a $VO_{2max}$ or $MET_{max}$.

9. The method according to claim 1, wherein the second parameter of the exercise intensity is a heart rate.

10. The method according to claim 1, wherein the at least one data subset comprises a first data subset, a second data subset and a third data subset, wherein the exercise threshold corresponding to the first data subset is a $VO_{2max}$ threshold, the exercise threshold corresponding to the second data subset is a LT2 (second lactate threshold) and the exercise threshold corresponding to the third data subset is a LT1 (first lactate threshold).

11. The method according to claim 1, wherein the at least one data subset comprises a first data subset and a second data subset, wherein the exercise threshold corresponding to the first data subset is a $VO_{2max}$ threshold and the exercise threshold corresponding to the second data subset is a LT2 (second lactate threshold).

12. The method according to claim 1, wherein the at least one data subset comprises a first data subset, wherein the exercise threshold corresponding to the first data subset is a $VO_{2max}$ threshold.

13. The method according to claim 1, wherein the data set comprises a first data subset and a second data subset, wherein each data subset of the first data subset and the second data subset comprises the plurality of values of the fitness performance level and the plurality of values of the exercise intensity in the state of the exercise threshold and respectively corresponding to the plurality of values of the fitness performance level, wherein the value of the exercise intensity in the state of the exercise threshold corresponding to the first data subset is larger than the value of the exercise intensity in the state of the exercise threshold corresponding to the second data subset if the exercise threshold corresponding to the first data subset and the exercise threshold corresponding to the second data subset are based on the same value of the fitness performance level.

14. The method according to claim 13, wherein the exercise threshold corresponding to the first data subset is a $VO_{2max}$ threshold.

15. The method according to claim 13, wherein the exercise threshold corresponding to the first data subset is a $VO_{2max}$ threshold and the exercise threshold corresponding to the second data subset is a LT2 (second lactate threshold).

16. The method according to claim 13, wherein the at least one mathematical correspondence comprises a first mathematical correspondence, wherein the first mathematical correspondence is determined based on the first data subset and the second data subset.

17. The method according to claim 16, wherein a first initial mathematical correspondence is determined based on the first data subset and a second initial mathematical correspondence is determined based on the second data subset, wherein the first mathematical correspondence is determined based on the first initial mathematical correspondence and the second initial mathematical correspondence.

18. A method for providing an exercise guiding, comprising:

determining, by a processing unit, a plurality of mathematical correspondences to divide a coordinate plane into a plurality of regions for defining a plurality of two-dimensional heart-rate zones, wherein the coordinate plane has a first axis based on a $VO_{2max}$ and a second axis based on a heart rate, wherein determining the plurality of mathematical correspondences comprises:

acquiring, from a memory unit, a data set comprising a first data subset, a second data subset and a third data subset, wherein the first data subset comprises a plurality of first values of the $VO_{2max}$ and a plurality of values of the heart rate in the state of a $VO_{2max}$ threshold respectively corresponding to the plurality of first values of the $VO_{2max}$, the second data subset comprises a plurality of second values of the $VO_{2max}$ and a plurality of values of the heart rate in the state of a LT2 (second lactate threshold) respectively corresponding to the plurality of second values of the $VO_{2max}$, and the third data subset comprises a plurality of third values of the $VO_{2max}$ and a plurality of values of the heart rate in the state of a LT1 (first lactate threshold) respectively corresponding to the plurality of third values of the $VO_{2max}$; and for each of the plurality of mathematical correspondences, performing, by the processing unit, a calculation based on the associating data thereof comprising at least one portion of a content of the data set;

transforming, by the processing unit, the plurality of two-dimensional heart-rate zones into a plurality of one-dimensional heart-rate zones of a current value of the $VO_{2max}$ for a user having the current value of the $VO_{2max}$; and providing, by the outputting unit, the exercise guiding for the user according to the plurality of one-dimensional heart-rate zones.

19. A method for providing an exercise guiding, comprising:
determining, by a processing unit, at least one mathematical correspondence to divide a N-dimensional space into a plurality of regions for defining a plurality of N-dimensional exercise training zones, wherein N is an integer and at least three, wherein the N-dimensional space has N−1 first axes respectively based on N−1 first parameters and a second axis based on a second parameter of an exercise intensity, wherein each two first parameters of the N−1 first parameters are different and one of the N−1 first parameters is the first parameter of a fitness performance level, wherein determining at least one mathematical correspondence comprises:
acquiring, from a memory unit, a data set comprising at least one data subset, wherein each data subset of the at least one data subset comprises a plurality of values of the fitness performance level and a plurality of sequences respectively corresponding to the plurality of values of the fitness performance level, wherein each of the plurality of sequences corresponds to the N−1 first parameters; and
for each of the at least one mathematical correspondence, performing, by the processing unit, a calculation based on the associating data thereof comprising at least one portion of a content of the data set;
transforming, by the processing unit, the plurality of N-dimensional exercise training zones into a plurality of one-dimensional exercise training zones of a current sequence of the N−1 first parameters for a user having the current sequence of the N−1 first parameters; and
providing, by the outputting unit, the exercise guiding for the user according to the plurality of one-dimensional exercise training zones.

20. The method according to claim 19, wherein the first parameter of the fitness performance level is a $VO_{2max}$ or $MET_{max}$.

* * * * *